US00PP24047P2

(12) United States Plant Patent
Graff

(10) Patent No.: US PP24,047 P2
(45) Date of Patent: Nov. 26, 2013

(54) ***HIBISCUS* PLANT NAMED 'ADONIS PEARL'**

(50) Latin Name: *Hibiscus rosa-sinensis*
Varietal Denomination: Adonis Pearl

(75) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 97 days.

(21) Appl. No.: 13/374,566

(22) Filed: Dec. 31, 2011

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — C. A. Whealy

(57) ABSTRACT

A new and distinct cultivar of *Hibiscus* plant named 'Adonis Pearl', characterized by its upright, mounding and bushy plant habit; glossy dark green-colored leaves; uniform and freely flowering habit; large white-colored flowers with dark red-colored centers; and excellent flower longevity.

3 Drawing Sheets

Botanical designation: *Hibiscus rosa-sinensis*.
Cultivar denomination: 'ADONIS PEARL'.

BACKGROUND OF THE INVENTION

The present invention relates to a new and distinct cultivar of *Hibiscus* plant, botanically known as *Hibiscus rosa-sinensis*, and hereinafter referred to by the name 'Adonis Pearl'.

The new *Hibiscus* plant is a product of a planned breeding program conducted by the Inventor in Sabro, Denmark. The objective of the breeding program is to create new strong *Hibiscus* plants with attractive and long-lasting flowers.

The new *Hibiscus* plant is a naturally-occurring branch mutation of *Hibiscus rosa-sinensis* 'Adonis', disclosed in U.S. Plant Pat. No. 21,592. The new *Hibiscus* plant was discovered and selected by the Inventor on a single flowering plant within a population of plants of 'Adonis' in a controlled greenhouse environment in Sabro, Denmark in April, 2009.

Asexual reproduction of the new *Hibiscus* plant by vegetative terminal cuttings in a controlled greenhouse environment in Sabro, Denmark since August, 2009 has shown that the unique features of this new *Hibiscus* plant are stable and reproduced true to type in successive generations.

SUMMARY OF THE INVENTION

Plants of the new *Hibiscus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Adonis Pearl'. These characteristics in combination distinguish 'Adonis Pearl' as a new and distinct *Hibiscus* plant:

1. Upright, mounding and bushy plant habit.
2. Glossy dark green-colored leaves.
3. Uniform and freely flowering habit.
4. Large white-colored flowers with dark red-colored centers.
5. Excellent flower longevity.

Plants of the new *Hibiscus* can be compared to plants of the parent, 'Adonis'. Plants of the new *Hibiscus* differ primarily from plants of 'Adonis' in flower bud and petal color as of plants of 'Adonis' have red purple-colored flower buds and petals.

Plants of the new *Hibiscus* can be compared to plants of the *Hibiscus rosa-sinensis* 'Cairo White', not patented. In side-by-side comparisons conducted in Sabro, Denmark, plants of the new *Hibiscus* differed from plants of 'Cairo White' in the following characteristics:

1. Plants of the new *Hibiscus* were more uniform in plant growth, bud development and time to flower than plants of 'Cairo White'.
2. Plants of the new *Hibiscus* had broader flower buds than plants of 'Cairo White'.
3. Flowers of plants of the new *Hibiscus* lasted about three to four days whereas flowers of plants of 'Cairo White' lasted a single day.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of a typical flowering plant of 'Adonis Pearl' grown in a container.

The photograph on the second sheet is a close-up view of developing flower buds and an open flower of 'Adonis Pearl'.

The photograph on the third sheet is a close-up view of a dissected flower of 'Adonis Pearl'.

DETAILED BOTANICAL DESCRIPTION

The aforementioned photographs and following observations, measurements and values describe plants grown during the summer in 13-cm containers in a glass-covered greenhouse in Sabro, Denmark and under environmental conditions and cultural practices which closely approximate commercial *Hibiscus* production. During the production of the plants, day temperatures ranged from 20° C. to 25° C., night temperatures ranged from 19° C. to 21° C. and light levels ranged from 40 to 50 klux. Plants were pinched one time about eight weeks after planting and were 21 weeks old when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Adonis Pearl'.

Parentage: Naturally-occurring branch mutation of *Hibiscus rosa-sinensis* 'Adonis', disclosed in U.S. Plant Pat. No. 21,592.

Propagation:

*Type*.—By vegetative terminal cuttings.

*Time to initiate roots, summer*.—About three weeks at temperatures of 24° C.

*Time to initiate roots, winter*.—About four weeks at temperatures of 24° C.

*Time to produce a rooted young plant, summer*.—About seven weeks at temperatures of 24° C.

*Time to produce a rooted young plant, winter*.—About nine weeks at temperatures of 24° C.

*Root description*.—Medium in thickness, fleshy; color, close to 158A.

*Rooting habit*.—Freely branching; dense.

Plant description:

*Plant and growth habit*.—Upright, mounding and bushy plant habit; moderately vigorous growth habit.

*Branching habit*.—Freely branching habit with usually about four to six lateral branches developing per plant; pinching enhances lateral branch development.

*Plant height*.—About 35 cm to 55 cm.

*Plant diameter* (*area of spread*).—About 30 cm to 50 cm.

Lateral branch description:

*Length*.—About 15 cm to 25 cm.

*Diameter*.—About 3 mm to 6 mm.

*Internode length*.—About 1 cm to 5 cm.

*Strength*.—Strong.

*Texture*.—Woody.

*Color*.—Close to N199A.

Foliage description:

*Arrangement*.—Alternate, single; numerous; symmetrical.

*Length*.—About 7 cm to 11 cm.

*Width*.—About 6 cm to 8 cm.

*Shape*.—Cordate.

*Apex*.—Acuminate.

*Base*.—Cordate.

*Margin*.—Crenate.

*Texture, upper and lower surfaces*.—Smooth, glabrous.

*Luster, upper surface*.—Glossy.

*Luster, lower surface*.—Matte.

*Venation pattern*.—Pinnate; arcuate.

*Color*.—Developing leaves, upper surface: Close to 135A. Developing leaves, lower surface: Close to 137C. Fully expanded leaves, upper surface: Close to N189A; venation, close to 138A. Fully expanded leaves, lower surface: Close to 137A; venation, close to 138B.

*Petiole*.—Length: About 3 cm to 5 cm. Diameter: About 2 mm. Texture, upper surface: Pubescent. Texture, lower surface: Smooth, glabrous. Color, upper and lower surfaces: Close to N199A.

Flower description:

*Flower arrangement*.—Flowers arranged singly at terminal leaf axils; uniform, continuous and freely flowering habit with numerous flower buds and open flowers per plant at one time; flowers face mostly upright to outwardly.

*Fragrance*.—None detected.

*Natural flowering season*.—Plants flower in the garden during the spring and summer or during periods of warm weather; in the greenhouse, plants can be flowered year-round; plants begin flowering about ten to twelve weeks after pinching.

*Flower longevity*.—Excellent flower longevity, flowers last for about three to four days; flowers persistent.

*Flower diameter*.—About 16 cm to 19 cm.

*Flower length* (*height*).—About 10 cm.

*Flower bud*.—Rate of opening: Flowers buds open in about two to three days. Length: About 7 cm to 9 cm. Diameter: About 2 cm to 4 cm. Shape: Ovate to lanceolate. Color: Between 3D and 10C.

*Petals*.—Arrangement: Corolla consists of five petals that are fused at base; petals imbricate. Length: About 10 cm to 11 cm. Width: About 9 cm to 10 cm. Shape: Fan-shaped. Apex: Rounded. Base: Attenuate. Margin: Entire, undulate. Texture, upper surface: Glabrous; rugose; velvety. Texture, lower surface: Glabrous; rugose; satiny. Color: When opening, upper surface: Close to 155A; towards the base, close to 46A. When opening, lower surface: Close to 11B to 11C. Fully opened, upper surface: Close to 155D; towards the base, close to 46A. Fully opened, lower surface: Close to 11D and 155B.

*Sepals*.—Appearance: Five sepals fused into a tubular star-shaped calyx. Length: About 3.5 cm. Width: About 1.3 cm. Shape: Lanceolate. Apex: Acuminate. Margin: Entire. Texture, upper surface: Rough. Texture, lower surface: Smooth. Color, upper surface: Close to 144A. Color, lower surface: Close to 146C.

*Peduncles*.—Length: About 3 cm to 4 cm. Diameter: About 3 mm. Strength: Strong. Texture: Smooth, glabrous. Color: Close to 137C.

*Reproductive organs*.—Androecium: Stamen number: Numerous, about 100. Filament length: About 3 mm. Filament color: Close to 155B. Anther shape: Rounded to ovate. Anther length: About 1 mm to 2 mm. Anther color: Close to 19A. Amount of pollen: Abundant. Pollen color: Close to 17A. Gynoecium: Pistil length: About 10 cm. Style length: About 9 cm. Style texture: Smooth, waxy. Style color: Close to 11D; towards the base, close to 53A. Stigma appearance: Five-parted, rounded. Stigma color: Close to 12A. Ovary color: Close to 145A.

*Seeds*.—Quantity produced per flower: About 1 to 15. Length: About 5 mm. Diameter: About 5 mm. Color: Close to 202A.

Temperature tolerance: Plants of the new *Hibiscus* have been observed to have tolerate temperatures from about 1° C. to about 35° C.

Pathogen & pest resistance: Plants of the new *Hibiscus* have not been observed to be resistant to pathogens and pests common to *Hibiscus*.

It is claimed:

1. A new and distinct *Hibiscus* plant named 'Adonis Pearl' as illustrated and described.

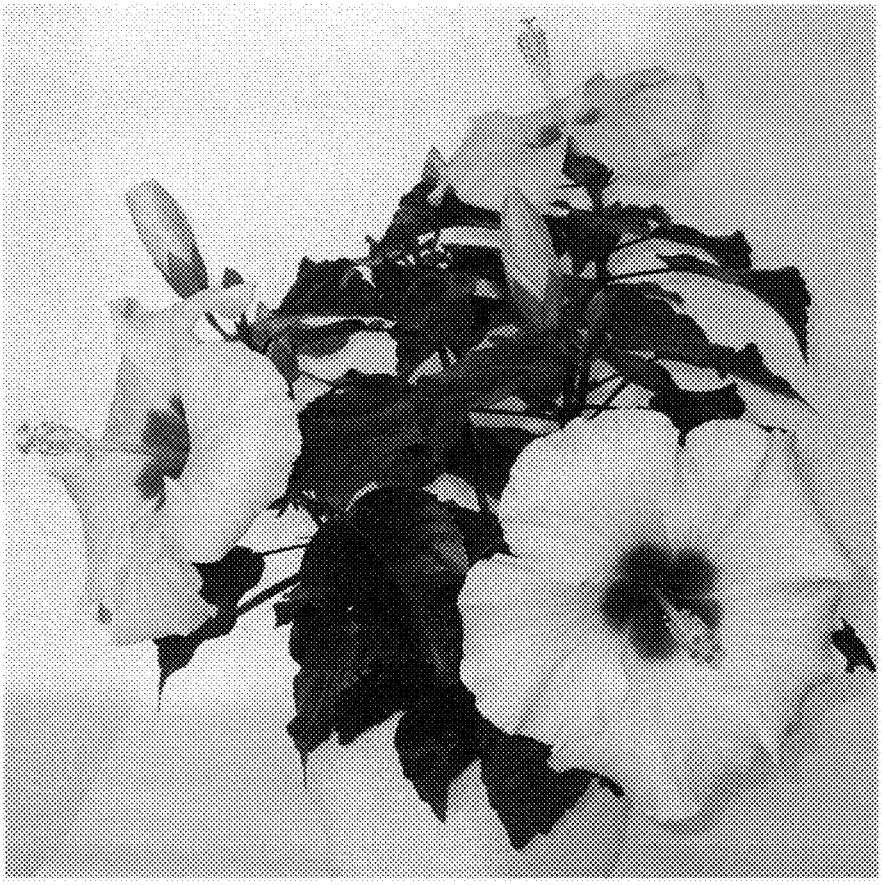

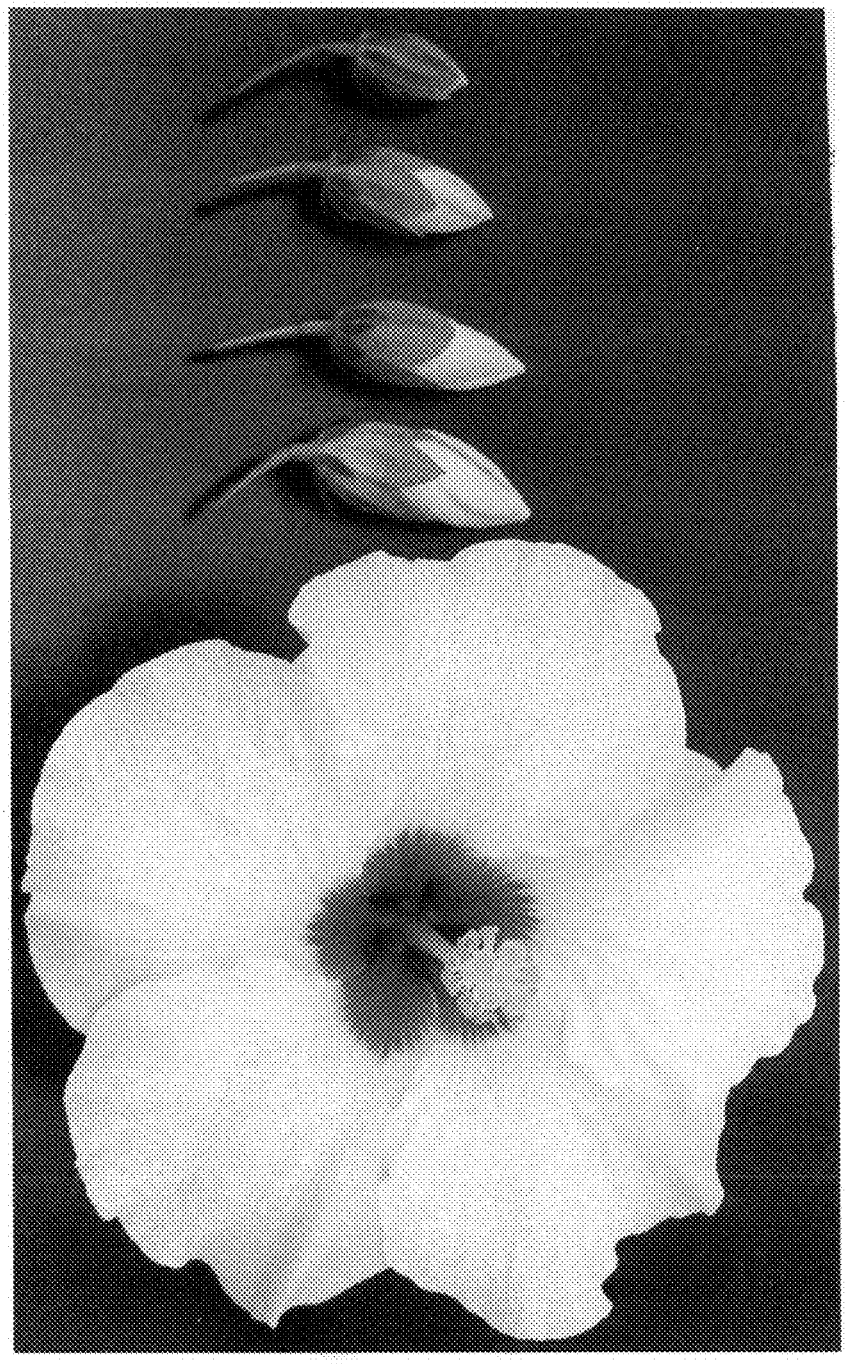

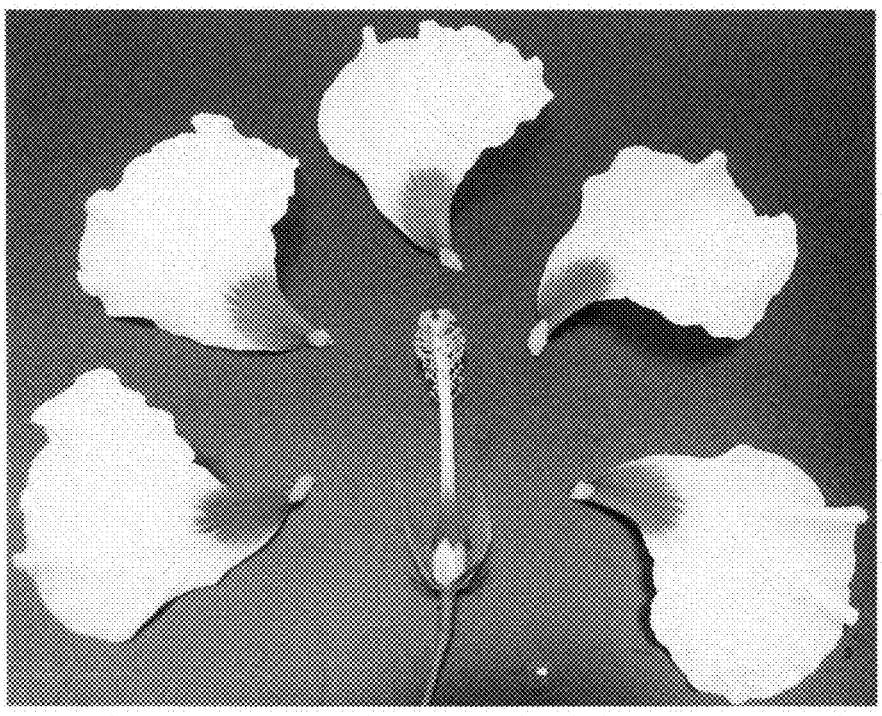

* * * * *